United States Patent
Errington

(10) Patent No.: US 6,759,209 B1
(45) Date of Patent: Jul. 6, 2004

(54) BACILLUS STRAIN AND ASSAY METHODS

(75) Inventor: Jeffrey Errington, Headington (GB)

(73) Assignee: ISIS Innovation Limited, Oxford (GB)

(*) Notice: Subject to any disclaimer, the term of this patent is extended or adjusted under 35 U.S.C. 154(b) by 0 days.

(21) Appl. No.: 09/831,546

(22) PCT Filed: Nov. 10, 1999

(86) PCT No.: PCT/GB99/03738

§ 371 (c)(1),
(2), (4) Date: Aug. 24, 2001

(87) PCT Pub. No.: WO00/28075

PCT Pub. Date: May 18, 2000

(30) Foreign Application Priority Data

Nov. 10, 1998 (GB) .............................. 9824682

(51) Int. Cl.[7] .............................. C12Q 1/18; C12Q 1/02
(52) U.S. Cl. .............................. 435/32; 435/6; 435/69.8; 435/243; 435/252.3; 435/252.31; 435/440
(58) Field of Search .............................. 435/32, 6, 69.8, 435/243, 252.3, 252.31, 440

(56) References Cited

U.S. PATENT DOCUMENTS

| | | | | |
|---|---|---|---|---|
| 3,888,978 | A | * 6/1975 | Duwel et al. | 424/199 |
| 5,891,667 | A | * 4/1999 | Hodgson et al. | 435/69.1 |
| 6,027,909 | A | 2/2000 | Errington | |
| 6,080,729 | A | * 6/2000 | Jaworski et al. | 514/44 |

FOREIGN PATENT DOCUMENTS

| | | |
|---|---|---|
| WO | 9205244 | 4/1992 |
| WO | 9700325 | 1/1997 |
| WO | 9826087 | 6/1998 |
| WO | 9826088 | 6/1998 |
| WO | 9918211 | 4/1999 |

OTHER PUBLICATIONS

Liao et al. Identification of a penicillin–binding protein 3 homolog, PBP3x, in *Pseudomonas aeruginosa*: gene cloning and growth phase–dependent expression. J Bacteriol. Mar. 1997; 179(5):1490–6.*
International Search Report in PCT/GB 99/03738.
International Preliminary Examination Report.
U.S. patent application No. 09/319777, filed Jun. 11, 1999, Now 6,350,587.
U.S. patent application No. 09/319778, filed Jun. 11, 1999, Now 6,255,065.

* cited by examiner

*Primary Examiner*—Anne-Marie Falk
*Assistant Examiner*—Daniel M. Sullivan
(74) *Attorney, Agent, or Firm*—Fulbright & Jaworski LLP

(57) ABSTRACT

Micro-organisms having a chromosome in which at least one gene has been partly or wholly replaced by a homologous gene from another micro-organism, and an artificially introduced reporter gene is present and is expressed in a manner related to a homologous gene expression product. Panels of such microorganisms are also described. Methods of assessing an agent for antibiotic activity and using the agent as an antibiotic. Methods of killing or inhibiting growth of bacteria.

32 Claims, No Drawings

BACILLUS STRAIN AND ASSAY METHODS

Whole-cell assays are known for specific inhibitors of *B. subtilis* proteins involved in chromosome partitioning and cell division. The property, of inhibiting chromosome partitioning and cell division, is indicative of actual or potential anti-microbial properties. The inventor has devised three such assays; they are described in WO 97/00325; WO 98/26087; and WO 98/26088, which are summarised below and to which reference is directed.

New compounds inhibitory for any chromosome partitioning and cell division functions are likely to have a broad spectrum of activity against a wide range of bacteria, including important pathogens, because the functions targeted appear to be highly conserved. However, it is possible that some of the compounds discovered may turn out to be relatively specific for the *B. subtilis* proteins, in which case they would not be useful general purpose antimicrobial agents.

A similar problem arises in any whole-cell assay for an inhibitor of a specific gene of any micro-organism. The problem is that an inhibitor of a specific gene of a particular strain or micro-organism, may be specific to that strain, or alternatively may have inhibitory properties which are exerted over a rather wide range of micro-organisms. The present invention addresses that problem by replacing a target gene in a micro-organism used for a whole cell assay with a homologous gene from a different organism, e.g. a micro-organism of more direct interest.

Thus the invention provides in one aspect a micro-organism having a chromosome in which:

a) at least one gene has been partly or wholly replaced by a homologous gene from another micro-organism, and b) an artificially introduced reporter gene is present and is expressed in a manner related to a homologous gene expression product.

In another aspect the invention provides a method of assessing an agent for antibiotic activity, which method comprises incubating the micro-organism as defined in the presence of the agent, and observing expression of the reporter gene or genes.

The micro-organism may be for example a yeast or more preferably a bacterium. The bacterium may be a Bacillus species that is capable of growth and sporulation under suitable conditions and for which genetic constructs can be made. *B. subtilis* is conveniently accessible and well characterised and is preferred.

A homologous gene is a functionally equivalent gene from another micro-organism. In the micro-organism of the present invention, at least one gene (the target gene) has been partly or wholly replaced by a homologous gene from another micro-organism. Preferably the target gene is one which is well conserved over many different species of bacteria or other micro-organisms. It is necessary that the homologous gene be functionally incorporated so as to be capable of expression in vivo. When the target gene is partly or wholly replaced by a homologous gene, it is necessary that the homologous gene be capable of forming an expression product that is different in some respect from the expression product of the target gene. Suitable target genes include genes involved in DNA replication, RNA synthesis, protein synthesis, cell wall synthesis, transport and cell division.

For micro-organisms which are Bacillus species e.g. *B. subtilis*, cell division genes include divIB (also called ftsQ), divIC, divIA, ftsA, ftsL (also called mraR), ftsZ, pbpB, as well as spoOJ and spoIIIE, and others, both known and to be discovered. Since these cell division genes are substantially conserved across many bacterial species, it is plausible that these engineered Bacillus strains will grow and sporulate with reasonable efficiency. The homologous gene may be taken from other bacilli or closely related organisms such as clostridia and Listeria. More preferably, the homologous gene may be taken from a pathogenic bacterium such as staphylococci and streptococci. *B. subtilis* molecular genetic methods make it straightforward to replace any gene with a homologous gene from another bacterium, An artificially introduced reporter gene is one which is not naturally present in the strain in question, and which may have been introduced by genetic manipulation. A reporter gene is one which on expression gives rise to an easily detected or observed phenotype. For example, the expressed protein may be an enzyme which acts on a substrate to give a product that is easily observed e.g. because it is coloured or chemiluminescent of fluorescent. Reporter genes capable of being expressed in Bacillus species and other micro-organisms are well known and documented in the literature. Reporter genes are preferably chosen so that their products can be readily assayed simultaneously. lacZ has been used for more than 10 years with great success in *B. subtilis* and there is a range of useful substrates that generate coloured or fluorescent products upon hydrolysis by β-galactosidase. The uidA gene of *E. coli* has recently been harnessed for similar purposes, and the range of substrates available for the gene product, β-glucoronidase is similar to that for β-galactosidase.

In one example, two different fluorogenic substrates are used to assay the activities of the two reporters simultaneously in a single reaction.

On incubation of the micro-organism, e.g. on cell division or sporulation, a reporter gene is expressed in a manner related to the activity of an expression product e.g. a cell division protein, of the homologous gene. For example, decreased activity of that protein may be associated with either increased expression or reduced expression of the reporter gene. When two reporter genes are used, preferably expression of one is increased, and expression of the other is decreased, in association with a change in the level of activity of that protein.

The preferred assay method of the invention involves inducing the Bacillus strain described to sporulate in the presence of a putative anti-microbial agent. Preferably the Bacillus strain is contacted, just prior to asymmetric cell division with the agent. To screen agents on a large scale, samples of the Bacillus strain may be cultured in an exhaustion medium to stimulate sporulation; either in the wells of a microtitre plate to which the agent is added; or in bulk to be dispensed into the wells of a microtitre plate of which individual wells contain one or more different agents. After suitable incubation, observation is made of expression of the one or more reporter genes. For example, when the expression products of two reporter genes are different enzymes, substrates for the two enzymes may be added to the wells of the microtitre plate, and observation made of e.g. chemiluminescent or fluorescent or coloured products of enzymatic activity.

Use of such strains have several practical consequences:

i) It enables inhibitors which act on the protein product of a pathogen but not on that of a parent micro-organism e.g. *B. subtilis* to be identified.

ii) In the case of an assay for inhibitors of cell division, it may facilitate identification of the specific target of the inhibitor. By screening promising compounds against a series of strains in which cell division genes have been systematically replaced with homologues from other organisms, the specific target of the inhibitory compound becomes evident. Thus, for example, detection of a compound which inhibits the B. subtilis parent strain but not a derivative carrying the S. aureus homologue of ftsZ, would be strongly suggestive of a compound targeted on the FtsZ protein.

iii) A panel of strains with a given target gene systematically replaced by genes from other organisms also provides information about the spectrum of activity of each potential inhibitor. For example, some of the compounds found to inhibit the B. subtilis SpoIIIE protein might not act on the strain bearing its S. aureus homologue. Other compounds might show non-species specific inhibition and act on a range of gene products from different organisms. Such tests provide a useful means of ensuring that new inhibitors have a broad spectrum of activities.

Thus in another aspect the invention provides a panel of the micro-organisms as defined, wherein in different members of the panel genes have been partly or wholly replaced by homologous genes from different micro-organisms. The invention also includes a method of assessing an agent for antibiotic activity, which method comprises incubating the members of the panel in the presence of the agent, and observing expression of the reporter gene or genes in different members of the panel. Also provided, is a method of killing or inhibiting the growth of bacteria, which method comprises contacting the bacteria with an agent which inhibits the growth of a micro-organism according to the invention.

According to WO 97/00325, a unique sporulation phenotype arising when spoIIIE is inactivated provides the potential for a very powerful and specific assay. In the absence of functional spoIIIE, the chromosome is trapped partially inside and partially outside the prespore compartment, but the prespore-specific transcription factor $\sigma_F$ is activated normally. Reporter genes dependent on $\sigma_F$ are expressed if they are located at certain places in the chromosome and blocked if they lie elsewhere. That invention provides a Bacillus strain having a chromosome with two reporter genes each linked to a promoter and responsive to the action $\sigma_f$ during sporulation, a first reporter gene being located in a segment of the DNA that is trapped in a prespore compartment when spoIIIE function is impaired, and a second reporter gene being located outside the said segment. An assay method using the Bacillus strain is also described.

The B. subtilis spoIIIE gene is required for translocation of the prespore chromosome through an asymmetrically positioned septum during sporulation in B. subtilis. Although at first sight this appears to be a very specialised mechanism, spoIIIE-like genes are highly conserved throughout bacteria. A more general function for the B. subtilis gene was revealed by experiments in which wild type and spoIIIE mutant cells of B. subtilis were exposed to sub-lethal concentrations of inhibitors of DNA replication (Sharpe and Errington, 1995, Proc. Natl. Acad. Sci. USA 92, 8630–8634). Under such conditions the probability of chromosomal DNA being caught in the division septum is increased. Wild type cells could recover from this state but in spoIIIE mutants the chromosome remained trapped and so these mutants were more sensitive to such inhibitors. If removal of chromosomal DNA from the division septum is the general function of SpoIIIE protein, and its action during sporulation just an extreme manifestation of this function, the spoIIIE-like genes from nonsporulating bacteria might be able to functionally complement the defect of spoIIIE mutants of B. subtilis and restore their ability to sporulate.

According to the present invention, the spoIIIE gene is partly or wholly replaced by a homologous gene from another bacterium. The use of the homologous gene from Streptococcus pneumoniae is described in the example below.

According to WO 98/26087, the effects of spoOJ mutations on prespore chromosome orientation, and the ability to detect this by use of a spoIIIE mutant background, provides the potential for a very specific whole-cell assay for inhibitors of spoOJ function. The presence of any given segment of chromosomal DNA in the prespore can be detected by use of a reporter gene controlled by a transcription factor $\sigma_F$, which is activated only in the small prespore compartment (a process that is not affected by perturbations in chromosome partitioning).

WO 98/26087 thus provides a Bacillius strain having a chromosome with the following modifications:
a) a mutation of a spoIIIE gene which blocks transfer of the prespore chromosome,
b) a mutation in the soj gene which prevents loss of spoOJ function from blocking sporulation, together with
c) a first reporter gene having a promoter which is dependent on $\sigma_F$ factor and placed at a location where impaired spoOJ function leads to increased trapping and hence to increased expression from the prespore, and/or
d) a second reporter gene having a promoter which is dependent on $\sigma_T$ factor and placed at a location where impaired spoOJ gene function leads to reduced trapping and hence to reduced expression in the prespore.

The present Invention provides a Bacillus strain of this kind in which the spoOJ gene has been replaced by its homologue from another bacterium.

Synthesis of a factor begins at the onset of sporulation, but its product is initially held in an inactive state by the action of an anti-$\sigma$ factor spoIIAB. Release from inhibition requires the concerted action of at least two other proteins, SpoIIAA and SpoIIE, which serve to allow release of $\sigma_F$ activity only after the sporulating cell has undergone asymmetric cell division and to restrict the $\sigma_F$ activity to the smaller prespore cell type. According to WO 98/26088, this dependence of $\sigma_F$ activation on septation is used as the basis for a sensitive assay for inhibitors of cell division. Thus that specification provides a Bacillus strain having two reporter genes, a first reporter gene having a promoter which is dependent on active $\sigma_F$ (or $\sigma_E$), and a second reporter gene having a promoter regulated similarly to the gene encoding the a factor, to provide a measure of the synthesis of the (inactive) a factor. A whole-cell screening method for identifying antimicrobial agents involves use of the Bacillus strain.

According to the present invention, any Bacillus cell division gene involved in these activities is partly or wholly replaced by a homologous gene from another bacterium. The Bacillus gene may be for example divIB (also called ftsQ), divIC, divIA, ftsA, ftsL (also called mraR), ftsZ, pbpB, as well as spoOJ and spoIIIE.

EXAMPLE

The inventors constructed a strain of B. subtilis in which the final 310 amino acid residues of the spoIIIE gene had been replaced with the equivalent section of the gene from Streptococcus pneumoniae strain R6, either in the correct or inverted orientation. In the correct orientation, the strain should make a hybrid protein comprising the poorly conserved membrane anchor region encoded by the B. subtilis gene fused to the highly conserved C-terminal coding region of the Streptococcus pneumoniae gene.

Strains with the Streptococcus gene inserted in either the correct or the inverted orientation, relative to the host spoIIIE gene, were induced to sporulate by a standard resuspension method, in parallel with an isogenic wild type strain. After 9 hours, the number of spores formed was measured on the basis of heat resistance, by heating at 80° C. for 10 min and then plating serial dilutions on nutrient agar. Colonies were counted after overnight incubation. In the strain with the Streptococcus DNA inserted in the inverted orientation, and so with no intact spoIIIE gene, sporulation was completely abolished (<10 heat resistant colony forming units [cfu] per ml of culture). However, with the Streptococcus DNA in the correct orientation, spore heat resistance was found to arise with approximately equal frequency ($2.0 \times 10_8$ cfu per ml) to the wild type ($1.3 \times 10_8$ cfu per ml). The outgrowth of a new colony from a heat resistant spore requires that the spore had acquired a complete chromosome. Thus, the hybrid gene must have been able to catalyse chromosome transfer into the spore compartment just as well as wild type SpoIIIE protein.

What is claimed is:

1. A Bacillus strain capable of growth and sporulation comprising:
   (a) a homologous spoIIIE gene from another bacterium partly or wholly replacing an endogenous spoIIIE gene; and
   (b) two reporter genes, wherein each reporter gene is operatively linked to a promoter and responsive to the action of $\sigma_F$ during sporulation; and wherein the first reporter gene is located in a segment of a DNA that is trapped in a prespore compartment when SpoIIIE function is impaired and the second reporter gene is located outside said DNA segment.

2. The Bacillus strain of claim 1, wherein the spoIIIE gene has been partly or wholly replaced by a homologous gene from *Streptoccus pneumoniae*.

3. The Bacillus strain of claim 1, wherein the Bacillus strain is a *B. subtilis*.

4. A method of assessing an agent for antibiotic activity comprising the steps of:
   incubating at least one Bacillus strain of claim 1, in the presence of the agent; and
   observing expression of the reporter gene or genes; wherein expression of only one of two reporter genes indicates that the agent acts as an antibiotic.

5. The method of claim 4, wherein the Bacillus strain is induced to sporulate in the presence of the agent.

6. The method of claim 4, wherein the Bacillus strain is induced to sporulate and is contacted with the agent just prior to asymmetric cell division.

7. A panel comprising a plurality of Bacillus stains of claim 1, wherein
   the spoIIIE gene of each Bacillus strain in the panel has been partly or wholly replaced by a homologous spoIIIE gene from different bacteria.

8. A method of assessing an agent for antibiotic activity comprising the steps of:
   a) incubating a panel of different Bacillus strain of claim 7, in the presence of the agent; and
   b) observing expression of the reporter gene or genes; wherein expression of only one of two reporter genes in a strain indicates that the agent acts as an antibiotic.

9. A method of determining whether an agent inhibits SpoIIIE function in Bacillus species, comprising the steps of:
   inducing the Bacillus strain of claim 1 to sporulate in the presence of the agent, and
   observing expression of the first and the second reporter gene, wherein expression of only one of two reporter genes indicates that the agent inhibits SpoIIIE function in Bacillus species.

10. A method of determining whether an agent inhibits the outgrowth of a bacterium comprising the steps of:
    incubating a Bacillus strain of claim 1 in the presence of the agent, and
    observing expression of the one or more reporter genes; wherein expression of only one of two reporter genes indicates that the agent inhibits the outgrowth of the Bacillus strain.

11. A method of preparing a composition for use in killing or inhibiting the outgrowth of bacteria comprising carrying out the method of claim 10 and formulating the agent identified as being capable of inhibiting the outgrowth of bacteria into a composition for use in inhibiting the outgrowth of bacteria.

12. A Bacillus strain capable of growth and sporulation comprising:
    a homologous cell division gene from another bacterium partly or wholly replacing a cell division gene; and
    two different reporter genes; wherein the first reporter gene has a promoter which is dependent on active $\sigma_F$ or $\sigma_E$ factor, and the second reporter gene provides a measure of the total synthesis of the $\sigma_F$ or $\sigma_E$ factor
    where the cell division gene replaced is selected from the group consisting of divIB, divIC, divIA, ftsA, ftsZ, ftsZ and pbpB.

13. The Bacillus strain of claim 12, wherein the Bacillus strain is a *B. subtilis* strain.

14. A method of assessing an agent for antibiotic activity, comprising the steps of:
    incubating at least one Bacillus strain of claim 12, in the presence of the agent; and
    observing expression of the reporter gene or genes; wherein reduced expression of the reporter gene which is dependent on active $\sigma_F$ or $\sigma_E$ factor is a measure of antibiotic activity.

15. The method of claim 14, wherein the Bacillus strain is induced to sporulate in the presence of the agent.

16. The method of claim 14, wherein the Bacillus strain is induced to sporulate and is contacted with the agent just prior to asymmetric cell division.

17. A panel comprising a plurality of Bacillus strains of claim 12, wherein the cell division gene of each Bacillus strain in the panel has been partly or wholly replaced by a homologous cell division gene from a different bacteria, where the cell division gene replaced is selected from the group consisting of diVIB, diVIC, divIA, ftsA, ftsL, ftsZ and pbpB.

18. A method of assessing an agent for antibiotic activity, comprising the steps of:
    incubating a panel of different Bacillus strain of claim 17, in the presence of the agent; and
    observing expression of the reporter gene or genes; wherein reduced expression of the reporter gene which is dependent on active $\sigma_F$ or $\sigma_E$ factor in a strain is measure of antibiotic activity.

19. A method of determining whether an agent inhibits cell division in Bacillus species, comprising the steps of:
    inducing the Bacillus strain of claim 12 to divide asymmetrically in the presence of the agent; and
    observing expression of the first and second reporter genes; wherein reduced expression of the reporter gene which is dependent on active $\sigma_F$ or $\sigma_E$ factor is a measure of cell division inhibition.

20. A method for determining whether an agent inhibits the outgrowth of a bacterium comprising the steps of:
(a) incubating a Bacillus strain of claim 12 in the presence of the agent; and
(a) observing expression of the one or more reporter genes; wherein reduced expression of the reporter gene which is dependent on active $\sigma_E$ or $94_E$ factor is a measure of outgrowth inhibition.

21. A method of preparing a composition for use in killing or inhibiting the outgrowth of bacteria, comprising carrying out the method of claim 20 and formulating the agent identified as being capable of inhibiting the outgrowth of bacteria into a composition for use in inhibiting the outgrowth of bacteria.

22. A Bacillus strain capable of growth and sporulation comprising;
a mutated spoIIIE gene, wherein the mutation results in blocking transfer of the prespore chromosome;
a homologous spoOJ gene from another bacterium partly or wholly replacing an endogenous spoOJ gene; and
one or two different reporter genes, wherein at least one reporter gene is operatively linked to a promoter which is dependent on $\sigma_F$ factor, and placed at a location wherein impaired SpoOJ function leads to increased trapping and increased expression in the prespore.

23. The Bacillus stain of claim 22, further comprising a mutated soj gene.

24. The Bacillus strain of claim 22, wherein the Bacillus strain is a *B. subtilis* strain.

25. A method of assessing an agent for antibiotic activity, comprising the steps of:
incubating at least one Bacillus strain of claim 22, in the presence of the agent; and
observing expression of the reporter gene or genes; wherein increased expression of one of the reporter genes indicates the agent acts as an antibiotic.

26. The method of claim 25, wherein the Bacillus strain is induced to sporulate in the presence of the agent.

27. The method of claim 25, wherein the Bacillus strain is induced to sporulate and is contacted with the agent just prior to asymmetric cell division.

28. A panel comprising a of plurality Bacillus strains of claim 22, wherein the spoOJ gene of each Bacillus strain in the panel has been partly or wholly replaced by a homologous SpoOJ gene from different bacteria.

29. A method of assessing an agent for antibiotic activity, comprising the steps of:
(a) incubating the panel of Bacillus strains of claim 28, in the presence of the agent; and
(b) observing expression of the reporter gene or genes; wherein increased expression of one of the reporter genes in a strain indicates the agent acts as an antibiotic.

30. A method of determining whether an agent inhibits SpoOJ function in Bacillus species, comprising the steps of:
inducing the Bacillus strain of claim 22 to divide asymmetrically in the presence of the agent; and
observing expression of the first and second reporter gene; wherein increased expression of one of the reporter genes indicates that the agent inhibits SpoOJ function.

31. A method for determining whether an agent inhibits the outgrowth of a bacterium comprising the steps of:
incubating a Bacillus strain of claim 22, in the presence of the agent; and
observing expression of the one or more reporter genes; wherein increased expression of one of the reporter genes indicates that the agent inhibits outgrowth.

32. A method of preparing a composition for use in killing or inhibiting the growth of bacteria, comprising carrying out the method of claim 31 and formulating the agent identified as being capable of inhibiting the outgrowth of bacteria into a composition for use in inhibiting the outgrowth of bacteria.

* * * * *